United States Patent [19]
Tarumi et al.

[11] Patent Number: 5,414,119
[45] Date of Patent: May 9, 1995

[54] HEXAFLUOROPROPYLENE OXIDE COMPOUNDS AND A METHOD OF MAKING SAME

[75] Inventors: Yasuo Tarumi; Noriyuki Koike; Toshio Takago, all of Gunma, Japan

[73] Assignee: Shin Etsu Chemical Co., Ltd., Tokyo, Japan

[21] Appl. No.: 203,250

[22] Filed: Mar. 1, 1994

[30] Foreign Application Priority Data

Mar. 2, 1993 [JP] Japan ................... 5-066020
Mar. 2, 1993 [JP] Japan ................... 5-066022

[51] Int. Cl.⁶ ................................ C07C 51/58
[52] U.S. Cl. ................................ 562/851; 568/415; 568/416
[58] Field of Search ............. 562/851; 568/415, 416

[56] References Cited

U.S. PATENT DOCUMENTS

| | | | |
|---|---|---|---|
| 3,114,778 | 12/1963 | Gerhard et al. | 260/614 |
| 3,274,239 | 9/1966 | Selmann | 260/514 |
| 3,311,658 | 3/1967 | Warnell | 260/544 |
| 3,322,826 | 5/1967 | Moore | 562/851 |
| 3,721,696 | 3/1973 | Sianesi | 562/851 |
| 4,081,466 | 3/1978 | Resnick | 260/544 F |
| 4,153,804 | 5/1979 | Yamabe et al. | 560/183 |

FOREIGN PATENT DOCUMENTS

| | | |
|---|---|---|
| 021861 | 1/1991 | Japan . |
| 2051831 | 5/1980 | United Kingdom . |
| 2053902 | 5/1980 | United Kingdom . |

Primary Examiner—Paul J. Killos
Attorney, Agent, or Firm—Millen, White, Zelano & Branigan

[57] ABSTRACT

Hexafluoropropylene oxide (HFPO) compounds, including polymers, expressed by the general chemical formula (1) below:

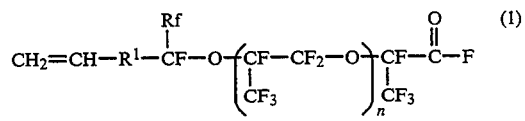

wherein $R^1$ is a single bond, an alkylene group of 1 to 10 carbon atoms, or said alkylene group in which a part of, or all of, the hydrogen atoms are substituted by fluorine atoms, Rf is a fluorine atom, a perfluoroalkyl group of 1 to 10 carbon atoms, or a perfluoroalkyl ether group, and n is 0 or an integer of at least 1. A manufacturing method for the HFPO compounds which is characterized by the reaction between hexafluoropropylene oxide and a vinyl group containing compound, expressed by the general chemical formula (2) below:

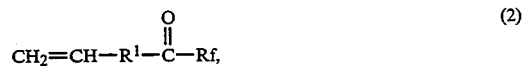

wherein $R^1$ and Rf are same as above. The compounds have utility as important intermediate raw materials for the production of novel functional silicone compounds having HFPO polymer units.

13 Claims, 2 Drawing Sheets

HEXAFLUOROPROPYLENE OXIDE COMPOUNDS AND A METHOD OF MAKING SAME

This invention relates to a hetero-bifunctional hexafluoropropylene oxide compound and a method of making thereof. The compound possesses two different functional groups, a vinyl group at one end of the molecular chain and a —COF group at the other. The invention is also directed to novel starting materials used to make the compounds.

BACKGROUND OF THE INVENTION

A polymer of hexafluoropropylene oxide (HFPO) can possess various groups at its terminals depending on the types of polymerization initiators used during the polymerization process. For example, HFPO polymers with the following groups at the ends of their molecular chains, i.e., terminals, are already known: $CF_3$—, $CF_3(CF_2)_4$—, $(CF_3)_2CF$—, $(CF_3)_2CF$—$CF(CF_3)$—, $FSO_2$—, $CH_3S$—, $CH_3OCO$—, and $ICF_2$—. The HFPO copolymers having these groups are reviewed in Angew. Chem. Int. Ed. Engl., 24, 161 (1985).

Further, carbonyl fluoride (U.S. Pat. No. 3,114,778), perfluoropentanoyl fluoride (DE-OS 2,614,333), hexafluoroacetone (U.S. Pat. No. 3,274,239), and perfluoromethyl isopropyl ketone (U.S. Pat. No. 3,274,239) have been used as the initiators. The HFPO polymers obtained by using these initiators are expressed by the formula below:

$$Rf'—O—(Y)_p—CF(CF_3)—COF$$

Wherein Rf' is a perfluoroalkyl group, Y is the HFPO unit expressed by —$CF(CF_3)$—$CF_2O$—, and p is either 0 or a positive integer. On one terminal of the molecular chain (the opposite terminal from the side where the —COF group is connected) is the perfluoroalkyl group, which is a non-functional group.

Further, HFPO polymers with a functional group introduced at one end of their molecular chains by utilizing specific acid fluorides as an initiator are also known. For example, British Patent No. 2,053,902 shows an example which utilizes $FSO_2$—$CF_2$—$CF_2$—COF as an initiator and the HFPO polymer obtained in this case is expressed by the formula below:

$$FSO_2—CF_2—CF_2—CF_2—CF_2—O—(Y)_p—CF(CF_3)—COF,$$

wherein Y and p are same as described above. This compound is understood as a hetero-bifunctional polymer with a functional group (—$FSO_2$) introduced at one end of the molecular chain. Various other initiators which lead to the hetero-bifunctional polymers are also known and examples thereof are:

| | |
|---|---|
| $CH_3S$—$(CF_2)_3$—COF | (British Patent 2,051,831), |
| $CH_3OOC$—$(CF_2)_4$—COF | (DE-OS 2,708,677), and |
| I—$CF_2$—COF | (U.S. Pat. No. 3,311,658). |

However, HFPO compounds and polymers with a vinyl group introduced as a terminal functional group at the end of the molecular chain have not been reported. The terminal functional groups of the known HFPO compounds and polymers do not include vinyl groups. Such compounds and polymers without terminal vinyl groups are incapable of combining with silicone compounds through hydrosilyation, which limits their use in the field of silicone chemistry.

On the other hand, a compound expressed by the equation below is known to possess a vinyl group:

$$CH_2=CH—CH_2O—CF_2—(Z)—COF,$$

wherein Z is —$CF(CF_3)$—$OCF_2$—$CF_2O$—$CF(CF_3)$—. This compound has a similar but distinct molecular structure to that of an HFPO polymer having a vinyl group at one end of the molecular chain. However, this compound is prepared through the reaction of a compound which possesses two —COF groups, expressed by the equation below:

$$FOC—(Z)—COF,$$

wherein Z is same as described above, with allyl bromide in the presence of cesium fluoride. This reaction has problems, both by offering a poor selectivity of products and by producing diallyl compounds as by-products.

Therefore, an object of this invention is to provide HFPO compounds and polymers having a vinyl group at their terminal end, and a manufacturing method thereof.

It is a further object to provide a novel vinyl group containing compounds useful as intermediates for the HFPO compounds or polymers.

Upon further study of the specification and appended claims, further objects and advantages of this invention will become apparent to those skilled in the art.

SUMMARY OF THE INVENTION

This invention is directed to hexafluoropropylene oxide compounds, including polymers, expressed by the general chemical formula (1) below:

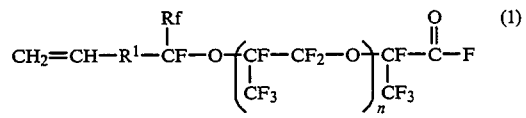

wherein $R^1$ is a single bond, an alkylene group preferably of 1 to 10 carbon atoms, or said alkylene group in which one or more of the hydrogen atoms are replaced by fluorine atoms, Rf is a fluorine atom, a perfluoroalkyl group preferably of 1 to 10 carbon atoms, or a perfluoroalkyl ether group, preferably of 2 to 10 carbon atoms, and n is 0 or an integer of 1 or more. group preferably of 1 to 10 carbon atoms, or a perfluoroalkyl ether group, preferably of 2 to 10 carbon atoms, and n is 0 or an integer of 1 or more.

Further, this invention is directed to a method for manufacturing the hexafluoropropylene oxide compounds expressed by general formula (1), which method is characterized by the reaction between hexafluoropropylene oxide (HFPO) and a vinyl group containing compound, expressed by the general chemical formula (2) below:

wherein $R^1$ and Rf are the same as described for formula (1), as a polymerization initiator.

Specific examples of the polymerization initiators expressed by the general chemical formula (2) are shown by the formulae below:

$CH_2=CHCF_2—COF$,
$CH_2=CH—(CF_2)_2—COF$,
$CH_2=CH—(CF_2)_3—COF$,
$CH_2=CH—(CF_2)_5—COF$,
$CH_2=CH—COF$,
$CH_2=CH—CH_2—COF$,
$CH_2=CH—CF_2—COCF_2—CF_3$,
$CH_2=CH—COCF_3$,
$CH_2=CH—CH_2—COCF_3$,
$CH_2=CH—CH_2—COCF_2—CF_3$,
$CH_2=CH—CF_2—COCF (CF_3)—OCF_2—CF_2—CF_3$,
$CH_2=CH—CF_2—COCF (CF_3)—OCF_2—CF (CF_3)—OCF_2—CF_2—CF_3$, and
$CH_2=CH—CH_2—COCF (CF_3)—OCF_2—CF_2—CF_3$.

The reaction between the vinyl group containing compounds and HFPO may be carried out, for example, by supplying the HFPO (a gas at the standard condition), while stirring, into a solution prepared by dissolving or dispersing the vinyl group containing compounds into an appropriate solvent along with a suitable catalyst in a catalytically effective amount.

Among the catalyst useful herein are, for example, alkali fluorides such as sodium fluoride, potassium fluoride, and cesium fluoride, and quaternary ammonium fluorides such as tetrabutyl ammonium fluoride and preferred amount of such catalyst is, in general, from 0.01 to 1.2 mol per 1 mol of the vinyl group containing compounds. However, this amount may be adjusted appropriately according to the amount of HFPO, such as when the reaction rate is low.

Preferred solvents are non-protonic polar solvents. Examples are glymes such as diglyme, triglyme, and tetraglyme, and nitriles such as acetonitrile, propionitrile, and adiponitrile. In general, it is preferred to use 1 to 100 weight parts of these solvents per 1 weight part of the vinyl group containing compound.

In general, the supply rate of HFPO is preferably from 0.02 to 3 mol/hour per 1 mol of vinyl group containing compounds. However, the entire amount of HFPO may be added at once when a pressure container is employed as a reaction vessel. The amount of HFPO added may be selected according to the desired molecular weight of the intended product compounds.

The reaction temperature is preferably from $-30°$ to $70°$ C. more preferably from $-30°$ to $30°$ C. A reaction temperature lower than $-30°$ C. will not allow the reaction to proceed effectively and one higher than $70°$ C. results in by-products, making it difficult to obtain the intended compounds.

After addition of HFPO, the reaction is continued for preferably another 1 to 5 hours, while stirring. Then the reaction mixture is recovered and the intended compounds are isolated. This isolation may be carried out by known methods, such as, for example, separation, extraction, and distillation.

Further, in this invention, the vinyl group containing compound expressed by the general formula (3) below:

$$CH_2=CH—R^1—CF—R_f, \quad \underset{O—M}{|} \tag{3}$$

wherein $R^1$ and Rf are the same as described for formula (1) and M is either a cesium or potassium atom, may be employed in place of the vinyl group containing compound expressed by the general chemical formula (2). The vinyl group containing compound expressed by the general chemical formula (3) may be obtained as a homogeneous solution, by mixing and stirring at least one mole, more preferably 1.0 to 1.3 mole, of cesium fluoride or potassium fluoride into a mixture of the vinyl group containing compounds expressed by the general formula (2) and a non-protonic polar organic solvent, followed by separation of the resultant precipitated excess of cerium or potassium fluoride. Subsequently, the HFPO compounds may be obtained by adding HFPO into the remaining solution and carrying out the reaction under conditions similar to those for the manufacture of HFPO compounds described previously.

The novel HFPO compounds of this invention possess a vinyl group at one end and a —COF group at the other. Therefore, utilization of these different functional groups makes various types of applications possible. For instance, a vinyl group enables the introduction of functional silicone groups through a hydrosilyation reaction and also allows performing of an addition polymerization reaction. Further, the —COF group can bind with various types of organic groups through ester and amide bondings. In addition, the HFPO compounds of this invention may be dimerized by light irradiation or converted to perfluorovinyl ethers by thermal decomposition. Combinations of such conversion reactions, which can take place at both ends of the novel HFPO compounds of this invention, make the compounds useful as, for example, important intermediate raw materials for the production of novel functional silicone compounds containing HFPO polymer units, which may be used, for example, as sealants and lubricants, among compounds containing HFPO polymer units, which may be used, for example, as sealants and lubricants, among others. According to this invention the novel HFPO compounds may be readily manufactured by the method disclosed herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding Japanese application No. 5-66,020 of Mar. 2, 1993 and Japanese application No. 5-66,022 of Mar. 2, 1993, are hereby incorporated by reference.

EXAMPLES

Example 1

After replacing the inside atmosphere of a 500 ml capacity three-neck flask equipped with a magnetic stirrer and a thermometer with nitrogen, 65.1 g of dried cesium fluoride and 447 g of dry tetraglyme were placed within. Then, 45.7 g of 2,2-difluoro-3-butenoyl fluoride was added into the flask and stirred for eight hours at room temperature (about $25°$ C.). After finishing the stirring, the flask was left quietly in order to precipitate the excess cesium fluoride. Then the supernatant liquid was extracted by suction and analyzed by the method of $^{19}$F-NMR. As a result, it was confirmed that this supernatant liquid is a tetraglyme solution with 16 wt. % of the compound expressed by the following chemical formula:

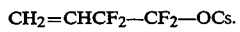

CH$_2$=CHCF$_2$—CF$_2$—OCs.

Then, the inside atmosphere of a one liter capacity flask which was equipped with a magnetic stirrer, a thermometer, a gas inlet tube, and a subzero cooling condenser, was replaced with nitrogen and 500 g of the tretraglyme solution prepared as above was placed within. While maintaining the temperature of the said flask at 2° C., a total of 114 g HFPO was introduced through the gas inlet tube slowly over the next 24 hours. After the addition of HFPO, the reaction mixture within the flask was stirred for another two hours. After the stirring, the reaction mixture was distilled under reduced pressure in order to recover a fraction (551 g) whose boiling point is at most 140° C. at the pressure of 2 mmHg. The distilled fraction was separated into two layers, thereafter, the bottom fraction was separated and recovered. The weight of the bottom fraction was 140 g. This fraction was analyzed by GC-MS, $^1$H-NMR, $^{19}$F-NMR and IR. A further distillation was required to provide a resultant fraction with a boiling point of 86.0° to 86.5° C. (at 760 mmHg) which was analyzed by the methods of $^1$H-NMR, $^{19}$F-NMR, and IR. By this second analysis, the product was confirmed to be the compound expressed by the formula (4) below:

$$\text{CH}_2=\text{CHCF}_2-\text{CF}_2-\text{OCFCOF} \quad (4)$$
$$\qquad\qquad\qquad\qquad\qquad |$$
$$\qquad\qquad\qquad\qquad\qquad \text{CF}_3$$

The combined results of both analyses are shown below.

GC-MS 271 (M-F)$^+$ $^1$H-NMR (TMS as standard) 5.9 ppm (m, 3H) $^{19}$F-NMR (CF$_3$—COOH as standard) −53.6 ppm (d, 1F, —OCF(CF$_3$)—) −40.8 ppm (s, 2F, =CH—CF$_2$—) −10.3 ppm (m, 2F, —CF$_2$—O—) −5.7 ppm (m, 3F, —CF$_3$) 102.1 ppm (s, 1F, —COF) IR: Spectrum (see FIG. 1) 1885 cm$^{-1}$ (C=O) 1660 cm$^{-1}$ (C=C)

The analytical results of the said bottom layer, including the compound of formula (4), revealed that this layer is a mixture of 2,2-difluoro-3-butenoyl fluoride, of the HFPO compounds which contain a vinyl group at the end expressed by the formula (5):

wherein s is an integer from 0 to 4, and of the HFPO polymer expressed by the formula (6):

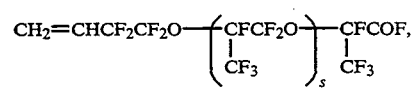

wherein t is an integer from 1 to 3.

The population ratio of these compounds, analyzed by GC, is listed in Table 1.

TABLE 1

| | | |
|---|---|---|
| 2,2-difluoro-3-butenyoyl fluoride | | 10.5% |
| HFPO compounds expressed by formula (5) | s = 0 | 21.3% |
| | s = 1 | 25.1% |
| | s = 2 | 18.4% |
| | s = 3 | 9.5% |
| | s = 4 | 1.2% |
| HFPO polymers expressed by formula (6) | t = 1 | 9.1% |
| | t = 2 | 3.6% |
| | t = 3 | 0.1% |

Example 2

First the inside atmosphere of a 50 ml capacity three-neck flask which was equipped with a magnetic stirrer, a thermometer, and a gas inlet tube, was replaced with nitrogen. Then, 0.12 g of dried potassium fluoride and 4.2 g of dry tetraglyme were placed within. Then, 4.0 g of 2,2-difluoro-3-butenoyl fluoride was added into the flask and stirred. While maintaining the temperature of the flask at 2° C. by cooling with an ice bath, a total of 6.6 g of HFPO was introduced through the gas inlet tube slowly over the next 13 hours. After the addition of HFPO, the reaction mixture within the flask was stirred for another one hour. After the stirring, the reaction mixture was quietly left at room temperature and 10.3 g of the fraction separated at the bottom was recovered. The analytical results of the bottom layer components determined similarly to Example 1, revealed a mixture of 2,2-difluoro-3-butenoyl fluoride, of the HFPO compounds having a vinyl group at the end expressed by the formula (5) wherein s is an integer from 1 to 10, however, and of the HFPO polymer expressed by the formula (6), wherein t is an integer from 1 to 8, however.

The population ratio of these compounds, analyzed by GC is listed in Table 2.

TABLE 2

| | | |
|---|---|---|
| 2,2-difluoro-3-butenoyl fluoride | | 16.8% |
| HFPO compounds expressed by formula (5) | s = 1 | 0.7% |
| | s = 2 | 1.2% |
| | s = 3 | 2.6% |
| | s = 4 | 5.0% |
| | s = 5 | 10.8% |
| | s = 6 | 10.8% |
| | s = 7 | 16.5% |
| | s = 8 | 15.9% |
| | s = 9 | 9.8% |
| | s = 10 | 4.2% |
| HFPO polymers expressed by formula (6) | t = 1 | — |
| | t = 2 | 2.4% |
| | t = 3 | 0.9% |
| | t = 4 | 1.5% |
| | t = 5 | 1.9% |
| | t = 6 | 1.7% |
| | t = 7 | 1.5% |
| | t = 8 | 0.7% |

Example 3

First the inside atmosphere of a 100 ml capacity three-neck flask which was equipped with a magnetic stirrer and a thermometer, was replaced with nitrogen. Then 9.1 g of dried cesium fluoride and 55.5 g of dry tetraglyme were placed within. Then, 8.4 g of 2,2-difluoro-3-butenoyl fluoride was added into the flask and stirred at room temperature (about 25° C.) for ten hours. After finishing the stirring, the flask was left quietly in order to precipitate the excess cesium fluoride. Then the supernatant liquid was extracted by suction and analyzed by the method of $^{19}$F-NMR. As a result, it was confirmed that this supernatant liquid is a tetraglyme solution with 23 wt. % of the compound expressed by the following chemical formula:

$$CH_2=CHCF_2-CF_2-OCs.$$

Then, the inside atmosphere of a 100 ml capacity flask which was equipped with a magnetic stirrer, a thermometer, a gas inlet tube, and a subzero cooling condenser, was replaced with nitrogen and 22.1 g of the tetraglyme solution prepared as above was placed within. While maintaining the temperature of the flask at $-28°$ C., a total of 11.9 g HFPO was introduced through the gas inlet tube slowly over the next 21 hours. After the addition of HFPO, the reaction mixture of 32.4 g was distilled under reduced pressure in order to recover the distilled fraction (28.0 g) of which boiling point is at most 200° C. at the pressure of 2 mmHg. The distilled fraction was separated into two layers, thereafter, the bottom fraction was further separated and recovered. The weight of the bottom fraction was 12.1 g. The components in the bottom layer were analyzed and they were:

| | |
|---|---|
| HFPO compounds expressed by the formula (5) (average s value, 3.6) | 90% |
| HFPO polymers expressed by the said formula (6) (average t value, 4.9) | 10% |

Example 4

After replacing the inside atmosphere of a 300 ml capacity three-neck flask equipped with a magnetic stirrer and a thermometer with nitrogen, 14.4 g of dried cesium fluoride an 187 g of dry tetraglyme were placed within. Then, 30 g of a polymerization initiator, expressed by the formula (7):

$$CH_2=CHCF_2-\overset{O}{\overset{\|}{C}}-\underset{CF_3}{\overset{|}{C}FO}-C_3F_7 \quad (7)$$

was added into the flask and stirred for four hours at room temperature (about 25° C.). After finishing the stirring, the flask was left quietly in order to precipitate the excess cesium fluoride. Then, the supernatant liquid was extracted by suction and analyzed by the method of $^{19}$F-NMR. As a result, it was confirmed that this supernatant liquid is a tetraglyme solution with 17 wt. % of the compound expressed by the following chemical formula (8):

$$CH_2=CHCF_2-\underset{C_3F_7O-CF-CF_3}{\overset{|}{C}F}-OCs. \quad (8)$$

Then, the inside atmosphere of a 300 ml capacity flask which was equipped with a magnetic stirrer, a thermometer, a gas inlet tube, and a subzero cooling condenser, was replaced with nitrogen and 209 g of the tetraglyme solution prepared as above was placed within. While maintaining the temperature of the flask at 2° C., a total of 24.7 g HFPO was introduced through the gas inlet tube slowly over the next 20 hours. After the addition of HFPO, the reaction mixture within the flask was stirred for another two hours. After the stirring, the reaction mixture was distilled under pressure in order to recover a fraction (53.6 g) whose boiling point is at most 130° C. at the pressure of 2 mmHg. The distilled fraction was separated into two layers, thereafter, the bottom fraction was further separated and recovered. The weight of the bottom fraction was 43.1 g. This fraction was analyzed by GC-MS, $^1$H-NMR and IR. Another distillation under reduced pressure was required to provide a resultant fraction with a boiling point of 103° to 107° C. (at 120 mmHg) which was analyzed by the methods of $^1$H-NMR, $^{19}$F-NMR, and IR. By this second analysis, the product was confirmed to be the compound expressed by the formula (9) below:

$$CH_2=CHCF_2CF-O-CF-COF. \quad (9)$$
$$\underset{C_3F_7O-CF-CF_3}{\overset{|}{\phantom{C}}} \quad \underset{CF_3}{\overset{|}{\phantom{C}}}$$

The results of the total of both analyses are shown below.

GC-MS 537 (M-F)+$^1$H-NMR (TMS as standard) 6.0 ppm (m, 3H) $^{19}$F-NMR (CF$_3$—COOH as standard) $-59.6$ ppm (m, 2F, —O—CF—CF—O—) $-52.3$ ppm (s, 1F, —O—CF—C(=O)—) $-51.8$ ppm (s, 2F, —CF$_3$—CF$_2$—) $-31.9$ ppm (m, 2F, =CH—CF$_3$—, —CF$_2$—O—) 103.6 ppm (s, 1F, —COF) IR: Spectrum (see FIG. 2) 1880 cm$^{-1}$ (C=O) 1660 cm$^{-1}$ (C=C)

The analytical results of the bottom layer, including the compound of formula (9), revealed that this layer is a mixture of the compound expressed by the formula (7), of the HFPO compounds which contain a vinyl group at the end expressed by formula (10):

$$CH_2=CHCF_2-\underset{C_3F_7O-CF-CF_3}{\overset{|}{C}FO}-\left[\underset{CF_3}{\overset{|}{C}FCF_2O}\right]_u-\underset{CF_3}{\overset{|}{C}FCOF} \quad (10)$$

wherein u is an integer from 0 to 5, and of the HFPO polymers expressed by the formula (6), wherein t is an integer from 1 to 5, however.

The population ratio of these compounds, analyzed by GC, is listed in Table 3.

TABLE 3

| | | |
|---|---|---|
| Compound expressed by formula (7) | | 17.3% |
| HFPO compounds expressed by formula (10) | u = 0 | 8.0% |
| | u = 1 | 12.9% |
| | u = 2 | 11.2% |
| | u = 3 | 5.9% |
| | u = 4 | 2.8% |
| | u = 5 | 1.5% |
| HFPO polymers expressed by formula (6) | t = 1 | 11.4% |
| | t = 2 | 4.6% |
| | t = 3 | 3.1% |
| | t = 4 | 1.0% |
| | t = 5 | 0.5% |

The preceding examples can be repeated with similar success by substituting the generically or specifically described reactants and/or operating conditions of this invention for those used in the preceding examples.

BRIEF DESCRIPTION OF THE DRAWINGS

Various other objects, features and attendant advantages of the present invention will be more fully appreciated as the same becomes better understood when considered in conjunction with the accompanying drawings in which like reference characters designate the same or similar parts throughout the several views, and wherein.

Figure 1:
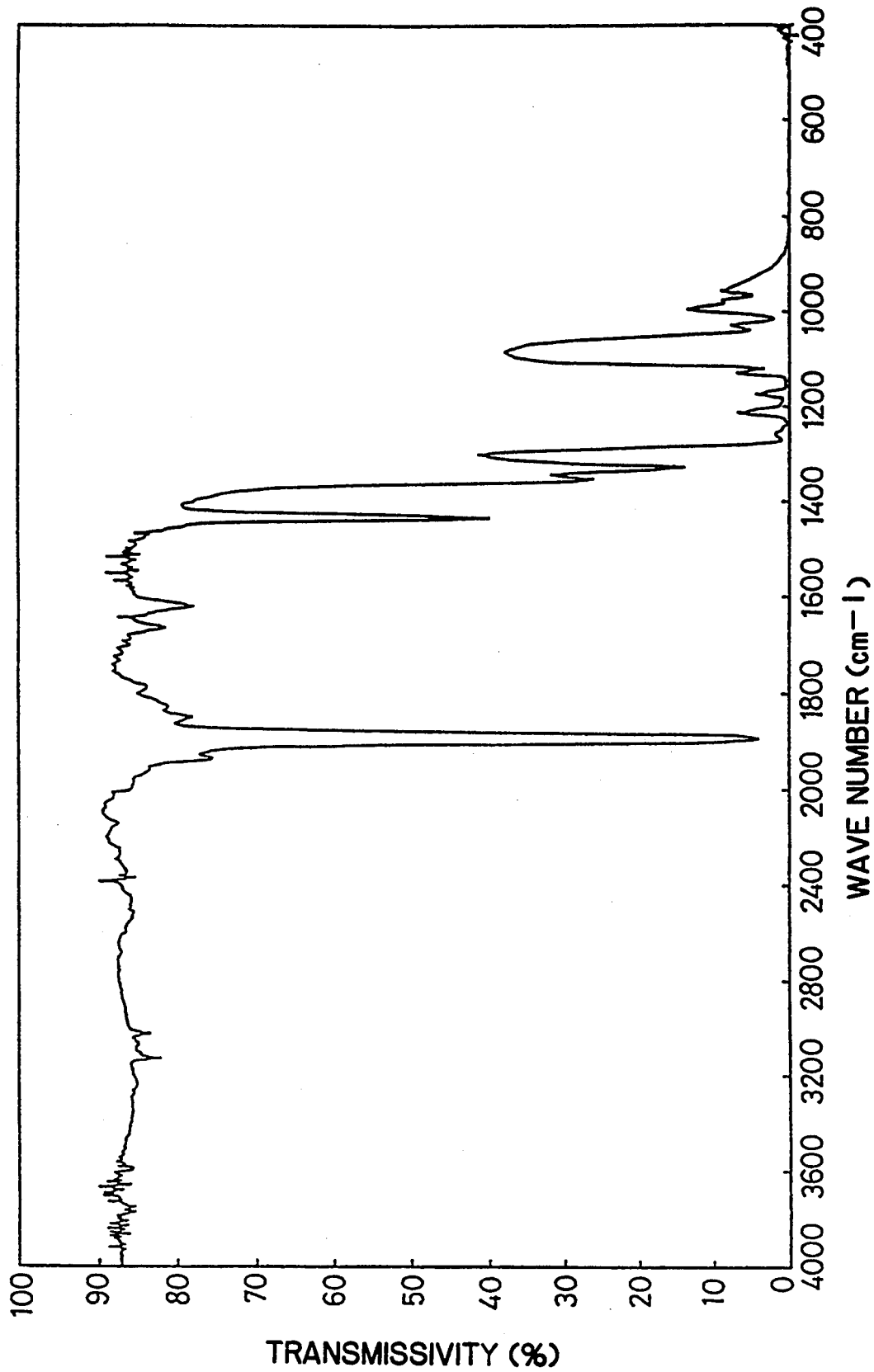
FIG. 1 is a chart of the IR absorption spectrum for the hexafluoropropylene polymer of this invention, obtained in Example 1.
Figure 2:
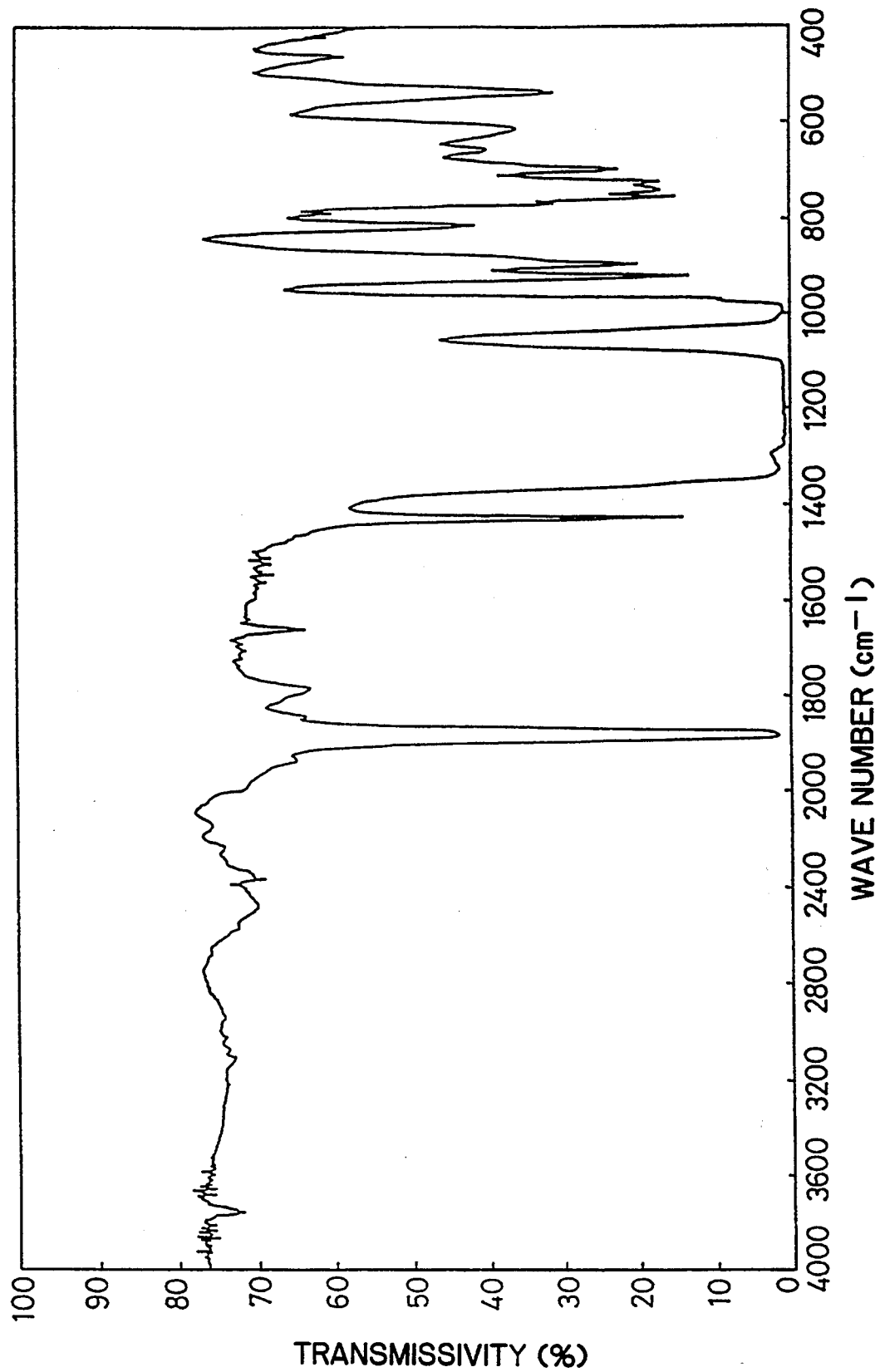
FIG. 2 is a chart of the IR absorption spectrum for the hexafluoropropylene polymer of this invention, obtained in Example 4.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A hexafluoropropylene oxide compound of the formula (1):

$$CH_2=CH-R^1-\overset{Rf}{\underset{|}{C}}F-O-\left(\overset{}{\underset{|}{C}F}-CF_2-O\right)_n\overset{}{\underset{|}{C}F}-\overset{O}{\underset{}{\overset{\|}{C}}}-F \quad (1)$$

wherein $R^1$ is a single bond, an alkylene group of 1 to 10 carbon atoms, or said alkylene group in which one or more of the hydrogen atoms are replaced by fluorine atoms, Rf is a fluorine atom, a perfluoroalkyl group of 1 to 10 carbon atoms, or a perfluoroalkyl ether group, and n is 0 or an integer of 1 or more.

2. The compound of claim 1, wherein $R^1$ is a single bond, $CH_2$, $CF_2$, $(CF_2)_2$, $(CF_2)_3$ or $(CF_2)_5$.

3. The compound of claim 1, wherein Rf is F, $CF_3$, $CF_2-CF_3$, $CF(CF_3)-O-CF_2-CF_2-CF_3$, or $-CF(CF_3)-O-CF_2-CF(CF_3)-O-CF_2-CF_2-CF_3$.

4. The compound of claim 1, wherein n is 0 or an integer of 1 to 100.

5. The compound of claim 1, wherein $R^1$ is an alkylene group of 1 to 10 carbon atoms in which all of the hydrogen atoms are replaced by fluorine atoms.

6. A method for preparation of the hexafluoropropylene oxide compound of claim 1, which comprises reacting hexafluoropropylene oxide and a vinyl group containing compound, of the formula (2) or (3):

$$CH_2=CH-R^1-\overset{O}{\overset{\|}{C}}-Rf, \quad (2)$$

$$CH_2=CH-R^1-\overset{O-M}{\underset{|}{C}F}-Rf, \quad (3)$$

wherein $R^1$ is a single bond, an alkylene group of 1 to 10 carbon atoms, or said alkylene group in which one or more of the hydrogen atoms are replaced by fluorine atoms, Rf is a fluorine atom, a perfluoroalkyl group of 1 to 10 carbon atoms, or a perfluoroalkyl ether group and M is a cesium or potassium atom.

7. The method of claim 6, wherein the reaction is carried out in the presence of a catalyst which is an alkali fluoride or a quaternary ammonium fluoride.

8. The method of claim 7, wherein the catalyst is potassium fluoride or cesium fluoride.

9. The method of claim 6, wherein the vinyl group containing compound is of the formula (2).

10. The method of claim 6, wherein the vinyl group containing compound is of the formula (3).

11. The method of claim 6, wherein the reaction is conducted in the presence of a solvent.

12. The method of claim 6, wherein the reaction is conducted in the presence of a non-protonic polar solvent.

13. A vinyl group containing compound of the formula (2):

$$CH_2=CH-R^1-\overset{O}{\overset{\|}{C}}-Rf, \quad (2)$$

wherein $R^1$ is a $-CF_2-$ group and Rf is a fluorine atom or a perfluoroalkyl or perfluoroalkyl ether group of the following formula:

$$-\underset{\underset{CF_3}{|}}{C}-(OCF_2\underset{\underset{CF_3}{|}}{C}F)_n-F$$

where n is a number 0 to 2.

* * * * *